United States Patent [19]
Baker et al.

[11] Patent Number: 5,522,889
[45] Date of Patent: Jun. 4, 1996

[54] APPARATUS AND METHOD FOR RESTORING EYELID FUNCTION

[75] Inventors: Robert S. Baker; Brian J. Willoughby; Robert R. Marshall, all of Lexington, Ky.

[73] Assignee: University of Kentucky Research Foundation, Lexington, Ky.

[21] Appl. No.: 372,734

[22] Filed: Jan. 13, 1995

[51] Int. Cl.$^6$ .................................................. A61F 2/14
[52] U.S. Cl. ................................................ 623/5; 128/898
[58] Field of Search ............................ 623/5; 128/897, 128/898

[56] References Cited

U.S. PATENT DOCUMENTS 3,940,803  3/1976  Weis, Jr. et al. .
4,955,910  9/1990  Bolesky ...................................... 623/13

FOREIGN PATENT DOCUMENTS 537679   1/1977  U.S.S.R. .
1725875  4/1992  U.S.S.R. .

*Primary Examiner*—Randy C. Shay
*Attorney, Agent, or Firm*—King and Schickli

[57] ABSTRACT

An apparatus is provided to restore eyelid function in a patient unable to voluntarily raise an eyelid. The apparatus includes a spiral torsion spring and pulley arrangement mounted in a housing that is implanted in the superior portion of the orbit of the eye. A wire connects the pulley to the eyelid. A spiral torsion spring provides the necessary spring force in tension to overcome the weight of the eyelid and draw the eyelid open. The natural muscles of eye closure are, however, sufficiently strong to overcome the spring tension thereby paying out wire from the pulley and closing the eye so as to provide normal blinking function. A position setting gear allows the biasing force of the spring to be selectively reduced sufficiently to allow the eye to remain closed for sleep or at other desired times. A method of treating ptosis is also disclosed.

16 Claims, 2 Drawing Sheets

APPARATUS AND METHOD FOR RESTORING EYELID FUNCTION

TECHNICAL FIELD

The present invention relates generally to the medical field and, more particularly, to an apparatus and method for restoring eyelid function in a patient suffering from ptosis; that is the inability to properly raise the eyelid.

BACKGROUND OF THE INVENTION

Ptosis, the drooping of the upper eyelid, is a condition that may be congenital or acquired. In congenital ptosis the levator palpebrae superioris muscle that elevates the lid is either absent or imperfectly developed. Acquired ptosis is usually due to injury or disease of the nerves that control the movements of the levator muscle. Ptosis may further be classified as myogenic, aponeurotic, neurogenic, mechanical or traumatic.

In most cases, surgery will be required to correct a ptotic lid. The surgical treatment is specifically adapted to address the underlying pathological condition. The amount of levator function present generally determines which surgical procedure will be adopted. For example, in myogenic ptosis, levator aponeurosis advancement or levator muscle resection has proven to be effective. In congenital ptosis, the resection of the levator may be done either externally or internally.

The levator aponeurosis advancement or muscle resection procedure is only useful when there is some function of the levator muscle. When levator function is essentially absent, the eyelid must be elevated or raised in some other way. The most often performed procedure at the present time is known as the frontalis suspension operation. In this procedure, the eyelid is suspended from the frontalis so that the eyelid is opened when the patient lifts the brow using the frontalis muscle. The connection may be made utilizing tendon tissue from the leg of the patient or synthetic material developed for this purpose. While this procedure allows the patient to open the eyelid and therefore see from the eye, it suffers from a number of drawbacks. The patient must adapt to the unnatural, sometimes tiring and uncomfortable movement of raising the brow to raise the eyelid. Further, the extent to which the patient is able to raise the lid, varies from procedure to procedure. Essentially, the procedure restores some eyelid function but that function is not natural. Of course, as the brow must be raised to raise the lid, this procedure is also a cosmetic failure. Thus, a need is identified for an improved procedure.

SUMMARY OF THE INVENTION

Accordingly, it is a primary object of the present invention to provide an apparatus and method overcoming the above-described limitations and disadvantages of the prior art to restore essentially normal eyelid function in patients unable to raise their lid due to a congenital or acquired condition.

Yet another object of the present invention is to provide a relatively simple, inexpensive and straightforward apparatus sufficiently compact to be readily implantable in the superior orbit of the eye yet providing reliable operation over an extended service life to allow a ptosis patient to regain essentially normal eyelid function.

Yet another object of the present invention is to provide a method and apparatus of restoring eyelid function in a patient suffering from ptosis or like symptoms whereby the eyelid is moved in a natural motion so as to restore substantially natural eyelid function while minimizing or eliminating undesired side effects so as to also provide a cosmetically acceptable and appealing solution to the ptosis problem.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved apparatus is provided for restoring eyelid function in a patient unable to voluntarily raise an eyelid. The apparatus may be generally described as including a housing, a means for biasing the eyelid to an open position and a means for connecting the biasing means to the eyelid.

More particularly, describing the invention, the biasing means includes a spring such as a spiral torsion spring that is operatively connected to a pulley. The pulley is mounted on bearings for relative rotation on a stub shaft attached to the housing. The connecting means is a medical grade wire that is capable of being received on the pulley. Thus, it should be appreciated that as the eyelid is raised, the wire is reeled in on the pulley and as the eyelid is lowered the wire is payed out from the pulley.

In practice, the tension force provided by the spiral torsion spring is of critical import to allow the restoration of natural eyelid function. More particularly, the tension force is selected so as to be sufficient to fully raise the eyelid. The tension force, however, must not be so great as to prevent coiling of the spring and closure of the lid when the functional weight of the lid increases as a result of the action of the muscles of eye closure when producing a blink. Thus, it should be appreciated that the spring force should be selected so as to be able to fully support between approximately 0.5–20.0 grams in tension.

Of course, it is also desirable to allow the eyelid to close naturally to allow sleep or rest periods as desired by the patient. Toward this end a means may be provided for selectively shifting the biasing means between (1) a first position/operating mode wherein the biasing force is provided on the eyelid so as to draw the eyelid open and allow normal eyelid function as just described and (2) a second position/operating mode so as to reduce the biasing force on the eyelid thereby allowing the eyelid to be maintained closed naturally for purposes of rest/sleep. This shifting means includes a position setting gear mounted for rotation relative to the stub shaft and a drive means, such as an electric motor, operatively connected to the position setting gear.

More particularly, the spiral torsion spring includes a first, inner end connected to the position setting gear and a second outer end connected to the pulley. Preferably, the position setting gear has an outer diameter of between substantially 3.0–6.0 mm while the pulley has an outer diameter of between substantially 5.0–12.0 mm so that the ratio of the outer diameter of the position setting gear to the outer diameter of the pulley is between 1.6–4.0. In this way, the size of the apparatus may be minimized to allow comfortable implantation in the superior portion of the orbit of the eye while also maintaining the necessary length of travel to allow full raising and lowering of the lid and opening and closing, respectively, of the eye. Additionally, the outer diameter ratio between the setting gear and the pulley functions to multiply the movement of the drive motor: that is drive motor movements and, therefore, power requirements are minimized while achieving a greater range of movement of the pulley.

Motor function to select an operating mode may be activated in any way known in the art including, for example, a subcutaneous manually manipulated switch. As a result of this shifting feature, the patient may close his or her eyes as desired without the need of taping the lids closed against the biasing force of the spring. Further, by selective positioning it is possible to maintain the eye closed without maintaining the spring in a tightly coiled condition. Not only is this more convenient and satisfactory to the patient but it effectively serves to extend the functional life of the spring over time.

In order to further maintain the operation of the apparatus over a long service life, it should be appreciated that the housing is sealed against impregnation by biological fluids. Further, a bellows seal is provided. This seal is made from material that is substantially impervious to biological fluids. The bellows seal envelopes the wire and is sealed at one end around the opening in the housing through which the wire extends to connect to the pulley and at the other end around the anchoring tab that secures the wire to the eyelid.

In accordance with yet another aspect of the present invention, a method is provided for restoring eyelid function in a patient suffering from the inability to voluntarily raise the eyelid. The method includes the initial step of implanting a means for biasing the eyelid to an open position. Preferably, implantation takes place in a superior portion of the orbit of the afflicted eye of the patient. Advantageously, sufficient space exists in this cavity between the muscles that control eye movement and the portion of the skull defining the brow to comfortably accommodate the device. This positioning also functions to allow the lid to be drawn up in a direction and with a motion similar to that of the normal musculature. Accordingly, normal eyelid function is effectively restored and the eyelid performs its proper role of lubricating and protecting the eye. Alternatively, the biasing means could be implanted in other positions adjacent the eye as when a patient's orbital volume does not permit intraorbital implantation.

Next is the connecting of the biasing means to the eyelid. The method also includes the adjusting of the tension force provided by the biasing means. Specifically, the tension force must be sufficient to support the weight of the eyelid so as to normally maintain the eyelid in the open position while still allowing the eyelid to blink to a closed position when the muscles of eye closure function to produce a blink. Only in this way is it possible to effectively reanimate the eye, providing essentially full function while maintaining a natural cosmetic appearance.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification, illustrates several aspects of the present invention and together with the description serves to explain the principles of the invention. In the drawing.

Figure 1:
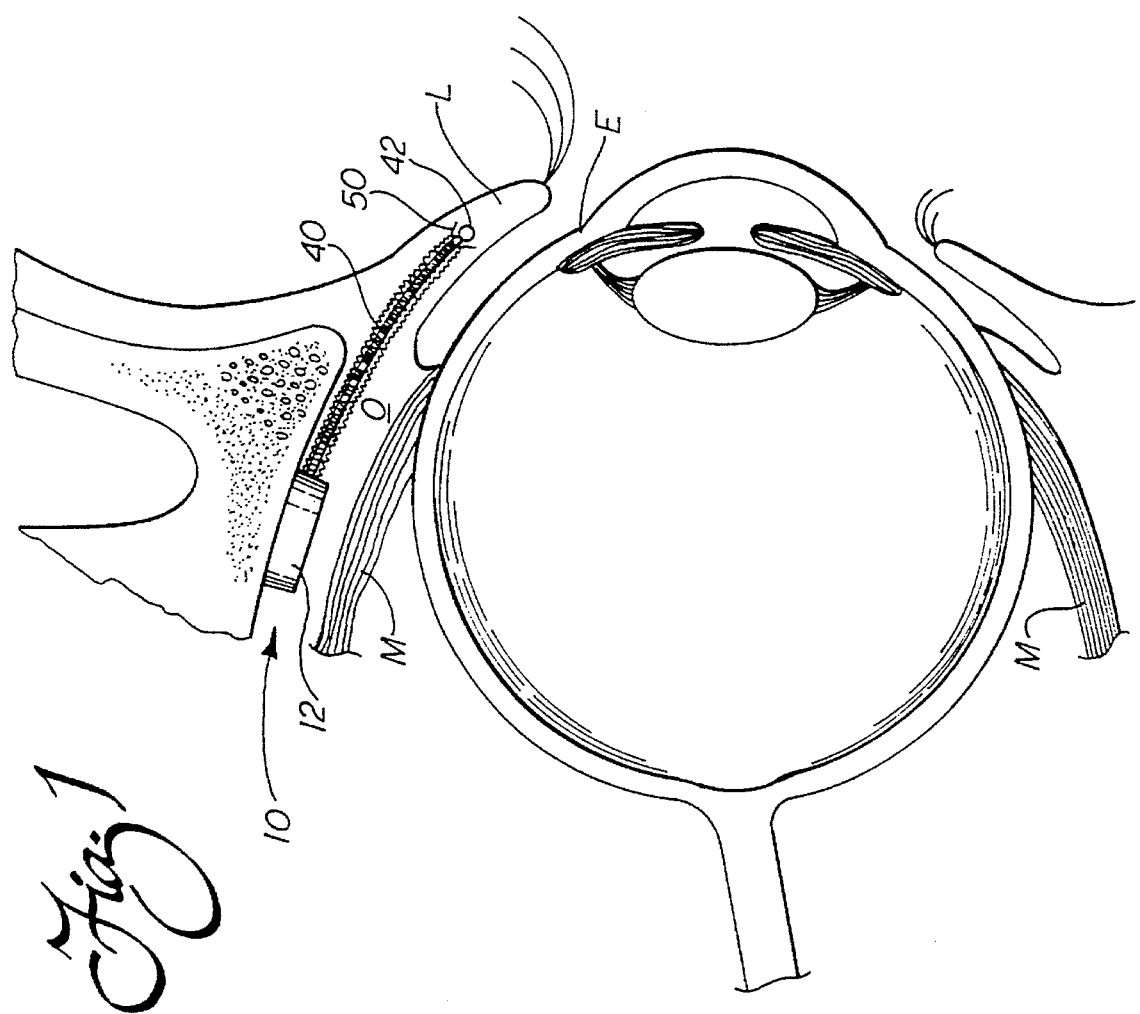
FIG. 1 is a schematical cross sectional view through the eye of a patient showing the relative implanted position of the apparatus of the present invention for restoring eyelid function.

Reference will now be made in detail to the present preferred embodiment of the invention, an example of which is illustrated in the accompanying drawing.

DETAILED DESCRIPTION OF THE INVENTION

Reference is now made to the drawing Figures showing the apparatus 10 of the present invention that is preferably implanted in a superior portion of the orbit O of the eye E to restore eyelid function in a patient suffering from an inability to fully raise the eyelid L, a condition also known as ptosis. Advantageously, this positioning effectively allows the apparatus 10 to move the eyelid L in the natural arc normally associated in a healthy individual with the muscle that serves this purpose. Accordingly, the apparatus 10 substantially restores natural eyelid movement and the associated lubricating and protecting functions the lid is adapted to provide to the eye E. Further, as substantially natural eyelid motion is restored and the apparatus 10 is fully implanted out of sight, the patient receives restored eyelid function through a means that is cosmetically almost undetectable to an observer. This very desirable cosmetic effect, now achieved for the first time when treating this affliction, greatly improves the patient's satisfaction as well as the patient's esteem/self confidence.

Figure 3:
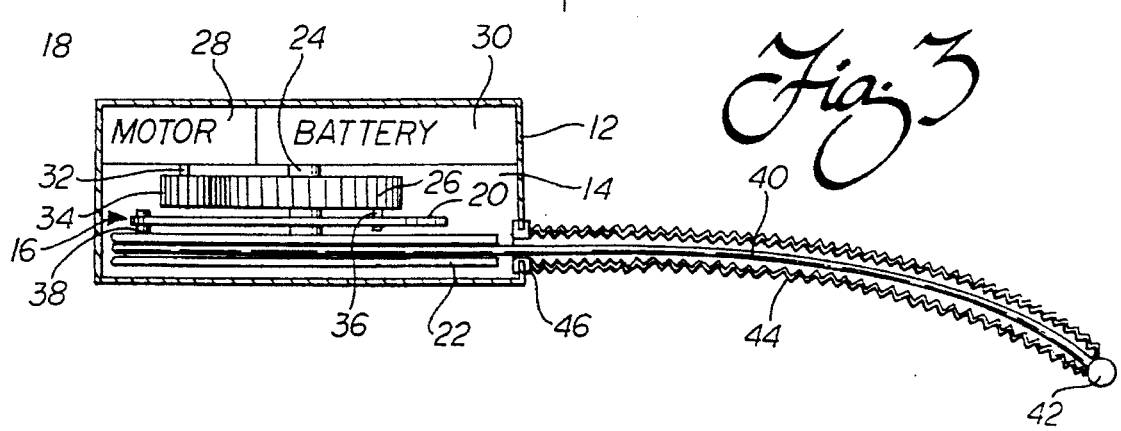
FIG. 3 is a schematical side elevational view showing the apparatus of the present invention.

As best shown in FIGS. 1 and 3, the apparatus 10 includes an outer housing 12 constructed from a substantially biologically inert material such as ceramic, titanium or stainless steel. The housing 12 is of relatively small size; that is, approximately 0.75 cm in diameter by 0.5 cm in thickness. Accordingly, the housing 12 is sufficiently compact to be implanted just inside the superior portion of the orbit O above the eye E between the muscles M that control eye movement. Specifically, the housing 12 may be fastened by one or more bone screws or other fastener (not shown) to the lower portion of the skull defining the brow.

As shown schematically in FIG. 3, the housing 12 includes an internal cavity 14 of three chambers for receiving: (1) a means for biasing the eyelid L to an opened position, generally designated by reference numeral 16; and (2) a means for selectively shifting the biasing means between a first position/operating mode wherein the biasing force is provided on the eyelid so as to draw the eyelid open and allow normal eyelid function and a second position/operating mode wherein the biasing force on the eyelid is reduced and the eyelid is maintained closed for rest/sleep. This selective shifting means is generally designated by the reference numeral 18.

More specifically, the biasing means 16 comprises a spiral torsion spring 20 connected to a cooperating pulley 22.

Preferably, the pulley includes an outer diameter of between 5.0–12.0 mm and a hub mounted by means of high quality jewel bearings 52 so as to allow rotation relative to a stationary stub shaft 24 mounted to or formed integral with the housing 12. The spiral torsion spring 20 is also centered about the stub shaft 24.

The selective shifting means 18 includes a setting gear 26 that is mounted for relative rotation of the stub shaft 24 again by means of high quality jewel bearings 52. The selective shifting means 18 also includes an electrical drive motor 28 and a power source such as a battery or batteries 30. The drive motor 28 is operatively connected to the setting gear 26 by means of a drive shaft 32 and drive gear 34. Of course, it should be appreciated that all the gears 26, 34, the pulley 22 and the spiral torsion spring 20 are preferably constructed from substantially biologically inert material. Further, the use of an electrical drive motor 28 to control the shifting of the apparatus 10 between operation modes is only presented for purposes of illustration and the invention should not be considered as limited thereto. Other mechanical, magnetic, electromechanical and electromagnetic devices could be utilized for this purpose. For example, a purely mechanical setting device could be used. Such a setting device could be implanted under the brow with easy access for the patient to manually set the apparatus 10 to either operating mode.

Figure 2:
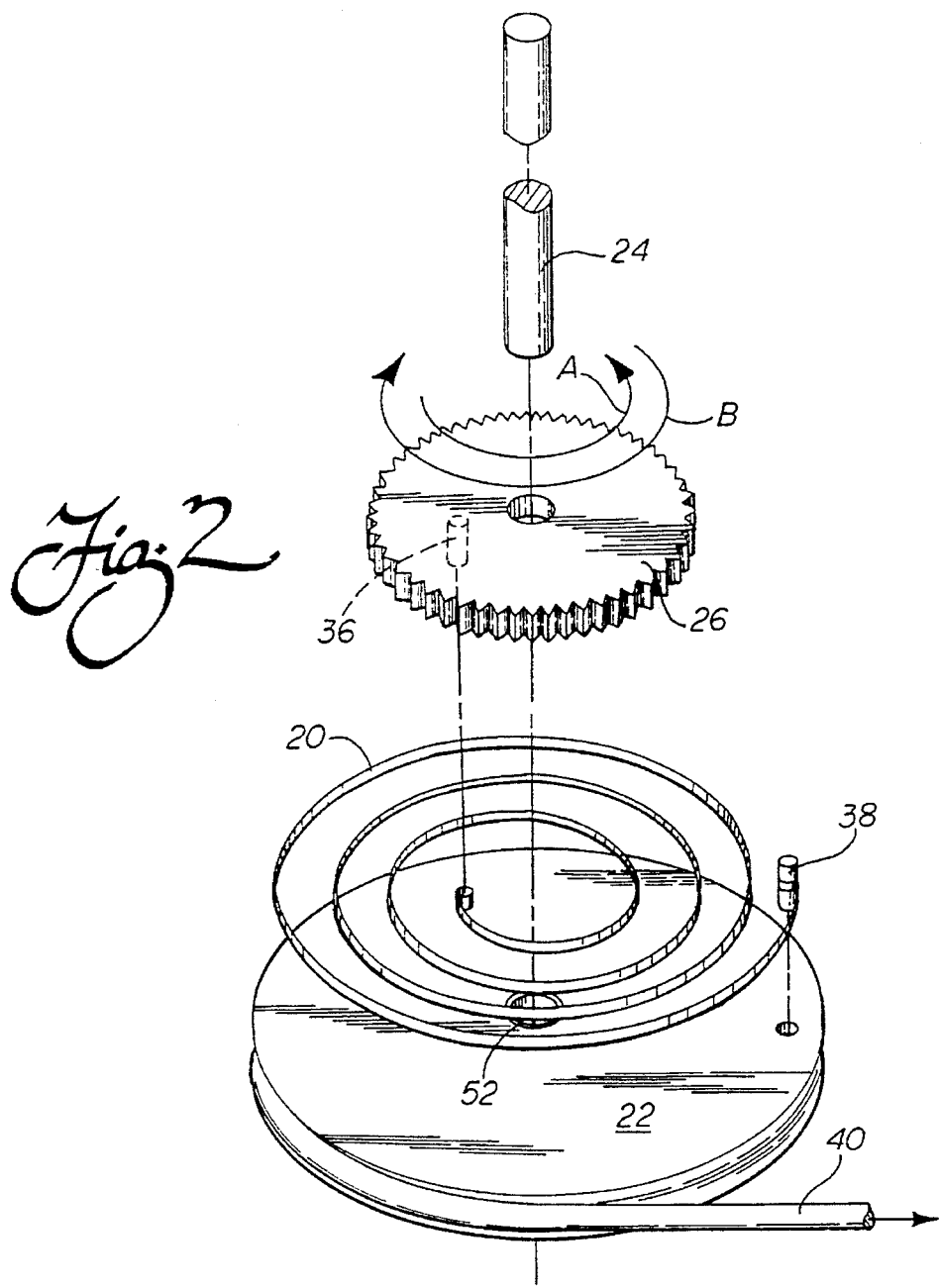
FIG. 2 is a detailed exploded view showing the relative inner connection and structural arrangement between the position setting gear, spiral torsion spring and pulley.

It should be further appreciated that the spiral torsion spring 20 is disposed between the setting gear 26 and pulley 22 about the stub shaft 24. The spiral torsion spring 20 includes a first, inner end operatively connected by means of a pin 36 or other fastener to the setting gear 26 and a second, outer end operatively connected by a means of a pin 38 or other means to the pulley 22 (see also FIG. 2). As will be described in greater detail below, this structural arrangement of the spiral torsion spring 20 allows the apparatus 10 to be selectively operated to provide essentially normal raising and lowering of the eyelid L during those alert periods of the day or night when that particular function is desired while still allowing the eyelid L to be fully closed over the eye E during sleep periods or at other desired times.

A fine, medical-grade wire 40 (e.g. polyurethane coated steel cable) connects the pulley 22 to the eyelid L. More particularly, the proximal end of the wire 40 is fastened to the pulley 22. The distal end of the wire 40 includes an enlarged head or anchoring tab 42 that is secured by nonabsorbable suture 50 or other means within the eyelid L. As shown in FIG. 1, the intermediate portion of the wire 40 extends between the outer and inner surfaces of the eyelid L and is received over the pulley 22. Accordingly, it should be appreciated that when the eyelid L closes, the wire 40 is payed out from the pulley 22 and when the eyelid opens, the wire is reeled in on the pulley. A bellows seal 44, formed from a flexible, biologically inert material may be provided enveloping the wire 40. As shown, the seal 44 also seals the opening 46 in the housing 12 through which the wire 40 extends from the pulley 22. In this way, the components received in the housing 12 are fully sealed and protected from the biological fluids that might otherwise inhibit their smooth and proper long term operation.

The method of restoring eyelid function in a patient suffering from ptosis involves the implanting of the apparatus 10 in a patient adjacent the afflicted eye. Preferably, the apparatus 10 is implanted in a superior portion of the orbit O of the afflicted eye E of the patient. The implanting is achieved by a delicate surgical procedure involving placing the patient under either general or local anesthesia. Next, the patients' eye and brow are prepared and draped in the usual orbital surgical fashion. An incision is made in either the inferior line of the brow or the lid crease and exposure of the periosteum overlying the brow ridge of the frontal bone is obtained by the combination of blunt and sharp dissection. Hemostasis is maintained at all steps of the procedure. An area the size of the prosthetic implant is cleared on the periosteum and the implant is secured to the bone with a bone screw, the hole for the screw being tapped prior to insertion of the screw.

When implanted, the housing is in an appropriate position on the orbital side of the frontal ridge with the wire from the device exiting in an inferior direction. This wire is then carried into the lid by use of a Wright needle and directed to the wire from a superior tarsal incision. The wire is secured to the tarsus in two or three sites by nonabsorbable suture 50. The lid height is set by choosing the length of wire appropriate to the individual patient's anatomy. The wounds are closed in layers, using suture appropriate to the patient's age. Recovery includes the application of topical antibiotic ointment.

Of course, it should be appreciated that some patients have insufficient orbital volume to allow clearance for the implantation of the apparatus 10 in the orbit. Under such circumstance, the apparatus 10 may be implanted in an alternative position such as just outside the orbit, underneath the eyebrow. A rigid guide tube is then provided to furnish a clear passageway for the connecting wire 40 to be secured in the eyelid L of the patient.

In order to provide proper function, the spring force provided by the spiral tension spring 20 must be carefully selected to meet the needs of each individual patient. More particularly, when the apparatus 10 is in the first position/operating mode to provide the biasing force necessary to draw the eyelid L open, the spring force must be sufficient to support the weight of the eyelid; that is the force must be sufficient to support between 0.5–20.0 grams in tension. The spring force, however, must not be so great that it is not overcome when the muscles of eye closure function to produce a blink. More specifically, when the muscles of eye closure operate, the spiral torsion spring 20 must coil sufficiently to allow the eyelid L to fully close and thereby provide the desired cosmetic and functional result. More specifically, blinking is a critical function that allows the eye E to be both more lubricated and protected. Further, the blinking must be achieved with adequate frequency to prevent the eye from drying and becoming sore. This blinking action must also be achieved with relevant ease for the comfort of the patient. Thus, it should be appreciated that the selection of the proper spring force is a critical aspect of the present invention.

Given that there is variability in both the weight of the lid and the power that each individual patient will have in lid closure, three different spring tensions should be available. Muscle power for lid closure is almost always much greater than the weight of the lid even in patients with relatively weak lid closure. However, some patients with congenital ptosis have relatively weak lid closure. The spring tension should be maximized in order to provide the most rapid lid rise possible. Therefore, a clinical assessment of lid closure power is made preoperatively by a clinician experienced in ptosis diagnosis and management. On the basis of this, a classification of lid closure as 1+, 2+, or 3+ is made. This corresponds to spring tensions of 10 grams, 15 grams, and 20 grams, with 20 grams representing power involved in normal reflexive lid closure.

With the apparatus 10 properly implanted, it is, of course, important that the patient be able to selectively shift or adjust the apparatus between the first position/operating mode wherein the biasing force is provided on the eyelid L so as to draw the eyelid open and allow normal eyelid function and the second position/operating mode wherein the biasing force on the eyelid is reduced so that the eyelid may be comfortably maintained closed for sleep. To achieve this end, the drive motor 28 is preferably operatively connected to a subcutaneous switch (not shown) that may be manually manipulated to control position/operating mode selection as desired by the patient.

More particularly, as noted above, when the apparatus 10 is in the first position/operating mode, the setting gear 26 is in a position so that the spiral torsion spring 20 provides the necessary spring force to maintain the eyelid L open at all times except when the muscles of eye closure function to provide a blinking action. At other times, however, such as during times of rest, the patient may wish to comfortably maintain the eyelid L closed. This can be accomplished by activating the drive motor 28 to rotate the setting gear 26 to the second position/operating mode. This rotation of the setting gear 26 causes the necessary reduction in the force of the tension spring 20 to allow the weight of the eyelid L to draw and maintain the eyelid closed.

More specifically, as pointed out above, it should be noted that the first, inner end of the spiral torsion spring 20 is operatively connected to the setting gear 26. Accordingly, relative rotation of the setting gear allows the adjustment of the spring force. Thus, it should be appreciated that rotation of the setting gear 26 in a counterclockwise direction (note action arrow A in FIG. 3) reduces the spring tension allowing the weight of the eyelid L to pull the eyelid closed for periods of rest and sleep. Alternatively, rotation of the setting gear 26 in the clockwise direction (note action arrow B in FIG. 3) increases the spring tension so that the spiral torsion spring 20 draws the eyelid L open. As pointed out above, however, it should be appreciated, that the spring force of the spiral torsion spring 20 may be overcome by the muscles of eyelid closure to provide a normal blinking function.

In order to further conserve the life of the batteries 30 and enhance the service life of the apparatus 10, it should be appreciated that the setting gear 26 has an outer diameter of between substantially 3.0–6.0 mm. Thus, the ratio of the outer diameter of the setting gear 26 to the outer diameter of the pulley 22 is between approximately 1.6–4.0 and more preferably approximately 3:1. A small movement of the setting gear 26, therefore, causes a much larger movement of the pulley 22 when measured linearly. The smaller required movement of the setting gear 26, as necessary to release the spring tension and allow eyelid closure during rest periods or restore the spring tension for normal eyelid function during alert periods, reduces motor running time thereby saving battery life. Further, it should be appreciated that the adjustment between the two positions/operating modes may be completed by rotating the setting gear through no more of an arc than approximately 15°–75°.

In summary, numerous benefits result from employing the concepts of the present invention. Advantageously, the present apparatus and method provide a significantly improved means for restoring eyelid function that is more functionally sound and cosmetically acceptable: that is, provides both substantially natural lubricating and protecting functions and appearance in operation. By carefully selecting the force of the spiral tension spring 20, it is possible to allow the eyelid L to blink with adequate frequency and ease so that lubrication reaches the eye and prevents soreness for patient comfort. Further, by adjustment of the setting gear 26 through means of the drive motor 28, drive shaft 32 and drive gear 34, it is possible to selectively reduce the spring force of the spiral tension spring 20 so as to allow the eyelid to remain closed through the rest or sleep period. This also enhances patient satisfaction as it eliminates any need to tape or otherwise physically fasten the eyelids closed. Further, this significantly limits or removes the strain on the spiral tension spring 20 so as better maintain the proper function of the spring over a longer service life.

The foregoing description of a preferred embodiment of the invention has been presented for purposes of illustration and description. It is not intended to be exhaustive or to limit the invention to the precise form disclosed. Obvious modifications or variations are possible in light of the above teachings. For example, a less sophisticated apparatus 10 could be provided that would not include the selective shifting means 18. In such an apparatus, the inner end of the spiral tension spring 20 would simply be operatively connected or pinned to the housing 12 and the apparatus would be permanently fixed in the equivalent of the first position/operating mode wherein the necessary spring force is provided to maintain the eyelid L open to provide normal eyelid function including blinking through operation of the eyelid closure muscles. In this alternative design of the apparatus 10, the eyelid L would be maintained closed during the rest or sleep period by tape or some other physical means for retaining the eyelid in the closed position against the spring force for the desired time.

The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

We claim:

1. An apparatus for implantation to restore eyelid function in a patient suffering from an inability to voluntarily raise the eyelid of the eye as desired, comprising:

a housing;

means for biasing the eyelid to an open position held in said housing; and means for connecting said biasing means to the eyelid.

2. The apparatus set forth in claim 1 wherein said biasing means includes a spring operatively connected to a pulley.

3. The apparatus set forth in claim 2, wherein said pulley is mounted on bearings for relative rotation on a stub shaft attached to said housing.

4. The apparatus set forth in claim 3, wherein said spring provides a force in tension capable of supporting between 0.5–20.0 grams.

5. The apparatus set forth in claim 4, wherein said pulley has an outer diameter of between substantially 5–12 mm.

6. The apparatus set forth in claim 5, wherein said connecting means is a medical grade wire and a suture for securing a distal end of said medical grade wire to the eyelid, said medical grade wire capable of being payed out from and reeled in on said pulley.

7. The apparatus set forth in claim 6, further including means for sealing said housing and wire from biological fluids.

8. The apparatus set forth in claim 7, wherein said sealing means is a bellows seal enveloping said wire and connected to said housing.

9. The apparatus set forth in claim 5, further including means for selectively shifting said biasing means between a first position/operating mode wherein biasing force is provided on the eyelid so as to draw the eyelid open and allow normal eyelid function and a second position/operating mode so as to reduce the biasing force on the eyelid and thereby allow the eyelid to remain closed for sleep.

10. The apparatus set forth in claim 9, wherein said shifting means includes a position setting gear mounted for rotation relative to said stub shaft and a drive means operatively connected to said position setting gear.

11. The apparatus set forth in claim 10, wherein said spring is a spiral torsion spring including a first, inner end connected to said position setting gear and a second, outer end connected to said pulley.

12. The apparatus set forth in claim 11, wherein said position setting gear has an outer diameter of between substantially 3–6 mm so that the ratio of the outer diameter of the position setting gear to the outer diameter of the pulley is between 1.6–4.0.

13. The apparatus set forth in claim 1, further including means for sealing said biasing means and said connecting means from biological fluid.

14. The apparatus set forth in claim 13, wherein said sealing means is a bellows seal enveloping said connecting means and connected to said housing holding said biasing means.

15. A method for restoring eyelid function in a patient suffering from ptosis, comprising the steps of:

implanting a means for biasing the eyelid to an open position adjacent an afflicted eye of a patient;

connecting the biasing means to the eyelid; and adjusting tension force provided by said biasing means to support the weight of the eyelid so as to normally maintain the eyelid in the open position while allowing the eyelid to blink to a closed position when muscles of eye closure function to produce a blink.

16. The method set forth in claim 15, including the step of selectively setting the biasing means in a first position so as to provide the tension force necessary to provide normal eyelid movement and function and in a second position so as to reduce the tension force and allow the eyelid to remain closed.

\* \* \* \* \*